(12) United States Patent  
Stukan et al.

(10) Patent No.: US 8,589,130 B2  
(45) Date of Patent: Nov. 19, 2013

(54) METHOD OF SELECTING ADDITIVES FOR OIL RECOVERY

(75) Inventors: Mikhail Stukan, Al-Khobar (SA); Patrice Ligneul, Al-Khobar (SA); Wael Abdallah, Al-Khobar (SA)

(73) Assignee: Schlumberger Technology Corporation, Sugar Land, TX (US)

( * ) Notice: Subject to any disclaimer, the term of this patent is extended or adjusted under 35 U.S.C. 154(b) by 595 days.

(21) Appl. No.: 12/616,486

(22) Filed: Nov. 11, 2009

(65) Prior Publication Data

US 2011/0112815 A1    May 12, 2011

(51) Int. Cl.  
*G06F 7/48*    (2006.01)

(52) U.S. Cl.  
USPC .............................................. 703/6; 73/64.55

(58) Field of Classification Search  
USPC ................. 703/6, 10; 73/61.43, 61.44, 64.47, 73/64.48, 64.52, 64.54, 64.55  
See application file for complete search history.

(56) References Cited

U.S. PATENT DOCUMENTS

| | | | |
|---|---|---|---|
| 4,411,802 A | 10/1983 | Lester et al. | |
| 4,414,120 A | 11/1983 | Malloy et al. | |
| 7,062,421 B2 | 6/2006 | Jacobson et al. | |
| 7,561,998 B2 | 7/2009 | Panga et al. | |
| 2005/0119837 A1* | 6/2005 | Prakash et al. | 702/27 |
| 2007/0038379 A1* | 2/2007 | Vaidehi et al. | 702/19 |
| 2009/0070085 A1 | 3/2009 | Gullapalli et al. | |
| 2009/0114387 A1 | 5/2009 | Horvath Szabo et al. | |
| 2010/0096129 A1* | 4/2010 | Hinkel et al. | 166/270.1 |
| 2011/0198101 A1* | 8/2011 | Sanders et al. | 166/402 |

OTHER PUBLICATIONS

Vasquez, U.O.M., et al., Calculating the surface tension between a flat solid and a liquid: a theoretical and computer simulation study of three topologically different methods, J. Math. Chem., 45, 2009, pp. 161-174.  
Connolly, M.J., et al, Explicit Hydrogen Molecular Dynamics Simulations of Hexane Deposited onto Graphite at Various Coverages, Langmuir, 24 (7), 2008, pp. 3228-3234.  
Peters, G.H. et al., Molecular Dynamics Simulations of the Melting of a Hexane Monolayer: Isotropic versus Anisotropic Force Fields, Langmuir, 12, 1996, pp. 1557-1565.  
Roth, M.W., et al., Phase transitions in hexane monolayers physisorbed onto graphite, Phys. Rev. B, 71, 155427, 2005, pp. 1-13.  
Pint, C.L. et al., Behavior of hexane on graphite at near-monolayer densities: Molecular dynamics study, Phys. Rev. B, 73, 85422, 2006, pp. 1-10.

(Continued)

*Primary Examiner* — Kamini S. Shah  
*Assistant Examiner* — Andre Pierre Louis  
(74) *Attorney, Agent, or Firm* — Bridget Laffey; Rachel E. Greene; Jakub Michna

(57) ABSTRACT

A method is described for selecting an additive for enhanced recovery from a subterranean hydrocarbon reservoir including the steps of using a set of parameters to determine, at a first level of molecular dynamic modeling, an effect of the additive on interfacial tension between a hydrocarbon and water/brine; using the effect of the additive on interfacial tension derived from the first level of molecular dynamic modeling to determine, at a second coarser level of molecular dynamic modeling wettability effects; and using the effect of the additive on interfacial tension derived from the first level of molecular dynamic modeling and the wettability effects derived from the second level of molecular dynamic modeling to determine at a third coarser level of molecular dynamic modeling imbibition or drainage effects.

12 Claims, 4 Drawing Sheets

(56) References Cited

OTHER PUBLICATIONS

Rogel, E., Simulation of Interactions in Asphaltene Aggregates, Energy & Fuels, 14, 2000, pp. 566-574.

Headen, T.F. et al., Evidence for Asphaltene Nanoaggregation in Toluene and Heptane from Molecular Dynamics Simulations, Energy & Fuels, 23, 2009, pp. 1220-1229.

Murgich, J., Molecular Simulation and the Aggregation of the Heavy Fractions in Crude Oils, Molecular Simulation, vol. 29 (6-7), Jun. 2003, pp. 451-461.

Stoyanov, S.R., et al., Modelling of bitumen fragment adsorption on Cu+ and Ag+ exchanged zeolite nanoparticles, Molecular Simulation, vol. 34, Nos. 10-15, Sep.-Dec. 2008, pp. 943-951.

Ortega-Rodriguez, A., et al., Molecular View of the Asphaltene Aggregation Behavior in Asphaltene-Resin Mixtures, Energy & Fuels, 17, 2003, pp. 1100-1108.

Boek, E.S., et al., Deposition of Colloidal Asphaltene in Capillary Flow: Experiments and Mesoscopic Simulation, Energy & Fuels, 22, 2008, pp. 805-813.

Kuznicki, T., et al., Molecular Dynamics Study of Model Molecules Resembling Asphaltene-Like Structures in Aqueous Organic Solvent Systems, Energy & Fuels, 22, 2008, pp. 2379-2389.

Aguilera-Mercado, B., et al., Mesoscopic Simulation of Aggregation of Asphaltene and Resin Molecules in Crude Oils, Energy & Fuels, 20, 2006, pp. 327-338.

Li., C., et al., Stability of water/toluene interfaces saturated with adsorbed naphthenic acids—A molecular dynamics—study, Chem. Eng. Sci., 62, 2007, pp. 6709-6715.

Zhang, J., et al., A molecular dynamic study of water/methane/propane, J. Phys. B: At. Mol. Opt. Phys, 42, 035302, 2009, pp. 1-7.

Chanda, J., et al., Molecular Dynamics Study of Surfactant Monolayers Adsorbed at the Oil/Water and Air/Water Interfaces, J. Phys. Chem. B 110, 2006, pp. 23482-23488.

Wu, R., et al., Molecular Dynamics Simulations of Ammonium Surfactant Monolayers at the Heptane/Water Interface, J. Phys. Chem. B, 113, 2009, pp. 12680-12686.

Shinoda, W., et al., Coarse-grained molecular modeling of non-ionic surfactant self-assembly, Soft Matter, 4, 2008, pp. 2454-2462.

Rekvig, L., et al., Molecular simulation of droplet coalescence in oil/water/surfactant system, J. Chem. Phys. 127, 134701, 2007, pp. 1-11.

Gupta, A., et al., Molecular modeling of surfactant covered oil-water interfaces: Dynamics, microstructure, and barrier for mass transport, J. Chem. Phys., 128, 234709, 2008, pp. 1-18.

Duan, B., et al., Description of Ionic Surfactant/Water System by Adjusting Mesoscopic Parameters, J. Phys. Chem. B, 113, 2009, pp. 8854-8859.

Kvamme, B., et al., Effects of solid surfaces on hydrate kinetics and stability, The Geological Society Special Publication, 319, 2009, pp. 131-144.

Guiwi, L., et al., Molecular dynamics simulation of adsorption of an oil-water-surfactant mixture on calcite surface, Per. Sci., 6, 2009, pp. 76-81.

Halverson, J.D., et al., Wetting of hydrophobic substrates by nanodroplets of aqueous trisiloxane and alkyl polyethoxylate surfactant solutions, Chem. Eng. Sci. 64, 2009, pp. 4657-4667.

Nijmeijer, M.J.P., et al., A molecular dynamics simulation of the Lennard-Jones liquid-vapor interface, J. Chem. Phys. 89, 6, Sep. 15, 1988, pp. 3789-3792.

Dimitrov, D.I., et al., Capillary Rise in Nanopores: Molecular Dynamics Evidence for the Lucas-Washburn Equation. Phys. Revlett., 99, 054501, Aug. 2007, pp. 1-4.

Martic, G., et al., A Molecular Dynamics Simulation of Capillary Imbibition, Langmuir, 18, 2002, pp. 7971-7976.

Ahadian, S., et al., A molecular dynamics approach to examine the kinetics of the capillary imbibition of a polymer at nanoscale, Colloid Polym Sci 287, 2009, pp. 961-967.

\* cited by examiner

METHOD OF SELECTING ADDITIVES FOR OIL RECOVERY

FIELD OF THE INVENTION

The invention relates to methods of selecting chemical additives to lower the rock wettability to oil and/or reduce the oil/brine interfacial tension using molecular dynamics modeling.

BACKGROUND

Crude oil occurs naturally in reservoir formation mostly as pressurized liquid, which is the main driving mechanism for hydrocarbon primary recovery where wells are drilled into underground reservoirs. Once the pressure is depleted, a significant portion of total amount of oil in the reservoir is left behind and thus only a fraction of the oil in the ground can be recovered. Secondary (waterflooding, natural gas reinjection, air injection, carbon dioxide injection) and even tertiary (surfactant, polymer flooding, thermal recovery and in-situ combustion) techniques are required to enhance the hydrocarbon recovery factor from reservoirs.

Waterflooding is probably one of the most common secondary recovery techniques. Aqueous fluids are injected at one or more points in the reservoir at a pressure sufficient to effect a displacement of the oil from the pores of the reservoir and to push the oil ahead of the water front to the production well or wells. This technique is adequate as long as the water is available in large quantities, cheap and maintains a high displacement efficiency. In general though waterflooding by itself has a poor displacement efficiency as a result of the high interfacial tension (IFT) between water and oil. IFT contributes to the capillary retention of the discontinuous oil phase and thereby prevents its displacement. Therefore, chemical additives such as surfactants, which are wetting agent s that lower the interfacial tension between fluids or substances, are added to the water flood to enhance oil recovery. Surfactant-based techniques are typically categorized as a tertiary recovery method to distinguish it from the usual waterflooding.

The use of chemical additives in aiding oil to move easily through the reservoir requires a fundamental understanding of the interaction chemistry of these additives with oil, salinity and rock heterogeneity. To examine such processes on a molecular level is beyond what the classical core flooding experiments can provide. An alternative approach that is used to minimize the costly and time consuming experimentation is molecular modeling, which provides detailed information about material at the molecular or atomistic level. Molecular modeling can be used to assess the effectiveness of chemical additives in oil recovery by understanding their fundamental role in the recovery of oil and then optimizing their use to improve it.

Molecular Dynamics modeling is already used in biology, pharmacology and catalyst research to gain a better understanding of the interactions taking place at molecular and sub-molecular levels and/or assess the efficiency of some molecules as medications.

Some of these known methods and further information relating to others modeling methods within and outside the field of hydrocarbon recovery can be found for example in the following references:

PATENTS AND PATENT APPLICATIONS

[US 2009/0070085 A1] Methods for performing simulation of surfactant flooding of a hydrocarbon reservoir
[U.S. Pat. No. 7,062,421 B2] Methods for predicting adhesive interactions using molecular modeling
[US 2009/0114387 A1] Methods for identifying compounds useful for producing heavy oils from underground reservoirs

PAPERS

[1] U. O. M. Vázquez, W. Shinoda, P. B. Moore, C. Chiu, S. O. Nielsen, Calculating the surface tension between a flat solid and a liquid: a theoretical and computer simulation study of three topologically different methods, *J. Math. Chem.*, 45, 161 (2009).
[2] M. J. Connolly, M. W. Roth, P. A. Gray, C. Wexler, Explicit Hydrogen Molecular Dynamics Simulations of Hexane Deposited onto Graphite at Various Coverages. *Langmuir*, 24, 3228 (2008).
[3] G. H. Peters, D. J. Tildesley, Molecular Dynamics Simulations of the Melting of a Hexane Monolayer: Isotropic versus Anisotropic Force Fields, *Langmuir*, 12, 1557 (1996).
[4] M. W. Roth, C. L. Pint, C. Wexler, Phase transitions in hexane monolayers physisorbed onto graphite, *Phys. Rev. B*, 71, 155427 (2005).
[5] C. L. Pint and, M. W. Roth, C. Wexler, Behavior of hexane on graphite at near-monolayer densities: Molecular dynamics study, *Phys. Rev. B*, 73, 85422 (2006).
[6] E. Rogel Simulation of Interactions in Asphaltene Aggregates, *Energy & Fuels*, 14, 566 (2000).
[7] T. F. Headen, E. S. Boek, N. T. Skipper, Evidence for Asphaltene Nanoaggregation in Toluene and Heptane from Molecular Dynamics Simulations, *Energy & Fuels*, 23, 1220 (2009).
[8] J. Murgich, Molecular Simulation and the Aggregation of the Heavy Fractions in Crude Oils, *Molecular Simulation*, 29, 451 (2003).
[9] S. R. Stoyanovab, S. Gusarova, A. Kovalenko, Modelling of bitumen fragment adsorption on Cu1 and Ag1 exchanged zeolite nanoparticles, *Molecular Simulation*, 34, 953 (2008).
[10] A. Ortega-Rodriguez, S. A. Cruz, A. Gil-Villegas, F. Guevara-Rodriguez, C. Lira-Galeana, Molecular View of the Asphaltene Aggregation Behavior in Asphaltene-Resin Mixtures, *Energy & Fuels*, 17, 1100 (2003).
[11] E. S. Boek, H. K. Ladva, J. P. Crawshaw, J. T. Padding, Deposition of Colloidal Asphaltene in Capillary Flow: Experiments and Mesoscopic Simulation, *Energy & Fuels*, 22, 805 (2008).
[12] T. Kuznicki, J. H. Masliyah, S. Bhattacharjee, Molecular Dynamics Study of Model Molecules Resembling Asphaltene-Like Structures in Aqueous Organic Solvent Systems, *Energy & Fuels*, 22, 2379 (2008).
[13] B. Aguilera-Mercado, C. Herdes, J. Murgich, E. A. Muller, Mesoscopic Simulation of Aggregation of Asphaltene and Resin Molecules in Crude Oils, *Energy & Fuels*, 20, 327 (2006).
[14] C. Li, Z. Li, P. Choi, Stability of water/toluene interfaces saturated with adsorbed naphthenic acids—A molecular dynamics study, *Chem. Eng. Sci.*, 62, 6709, (2007).
[15] J. Zhang, Y. Guo, Y. Yang, K. Kozielski, A molecular dynamic study of water/methane/propane, *J. Phys. B*, 42, 035302 (2009).

[16] J. Chanda, S. Bandyopadhyay, Molecular Dynamics Study of Surfactant Monolayers Adsorbed at the Oil/Water and Air/Water Interfaces, *J. Phys. Chem. B* 110, 23482 (2006).

[17] R. Wu, M. Deng, B. Kong, Y. Wang, X. Yang, Molecular Dynamics Simulations of Ammonium Surfactant Monolayers at the Heptane/Water Interface, *J. Phys. Chem. B*, 113, 12680 (2009).

[18] W. Shinoda, R. DeVaneb, M. L. Klein, Coarse-grained molecular modeling of non-ionic surfactant self-assembly, *Soft Matter*, 4, 2454 (2008).

[19] L. Rekvig, D. Frenkel, Molecular simulation of droplet coalescence in oil/water/surfactant system, *J. Chem. Phys.* 127, 134701 (2007).

[20] A. Gupta, A. Chauhan, D. I. Kopelevichc, Molecular modeling of surfactant covered oil-water interfaces: Dynamics, microstructure, and barrier for mass transport, *J. Chem. Phys.*, 128, 234709 (2008).

[21] B. Duan, X. Zhang, B. Qiao, B. Kong, X. Yang, Description of Ionic Surfactant/Water System by Adjusting Mesoscopic Parameters, *J. Phys. Chem. B*, 113, 8854 (2009).

[22] B. Kvamme, A. Graue, T. Buanes, T. Kuznetsova, G. Ersland, Effects of solid surfaces on hydrate kinetics and stability, *Geological Society Special Publication*, 319, 131 (2009).

[23] L. Guiwu, Z. Xuefen, S. Changjin, Y. Hong, Molecular dynamics simulation of adsorption of an oil-water-surfactant mixture on calcite surface, *Per. Sci.*, 6, 76 (2009).

[24] J. D. Halverson, C. Maldarelli, A. Couzis, J. Koplik, Wetting of hydrophobic substrates by nanodroplets of aqueous trisiloxane and alkyl polyethoxylate surfactant solutions, *Chem. Eng. Sci.* 64, 4657 (2009).

[25] M. J. P. Nijmeijer, A. F. Bakker, C. Bruin, and J. H. Sikkenk, A molecular dynamics simulation of the Lennard-Jones liquid-vapor interface, *J. Chem. Phys.* 89, 3789 (1988).

[26] D. I. Dimitrov, A. Milchev, K. Binder. Capillary rise in nanopores: Molecular dynamics evidence for the lucas-washburn equation. *Phys. Rev. Lett.*, 99, 054501 (2007).

[27] G. Martic, F. Gentner, D. Seveno, D. Coulon, and J. De Coninck. A molecular dynamics simulation of capillary imbibition. *Langmuir*, 18, 7971 (2002).

[28] S. Ahadian, Y. Kawazoe, A molecular dynamics approach to examine the kinetics of the capillary imbibition of a polymer at nanoscale, *Colloid Polym Sci* 287, 961 (2009).

Gullapalli et al. [US 2009/0070085 A1] proposed in their application to perform a numerical simulation of surfactant flooding during enhanced oil recovery of a given hydrocarbon. The method makes use of a relative permeability model that maintains the physical consistency in the brine-oil phase behavior. The patent of Jacobson et al. [U.S. Pat. No. 7,062,421 B2] relates to a process for using computerized molecular interaction modeling to predict the adhesive interaction between a substance and a polymer. The authors state that molecular modeling methods maybe used to predict and select optimal adhesion promoting monomers for use in latex polymer coatings, providing the best wet adhesion to alkyd-coated substrates. Further, molecular modeling methods can also be applied to predict substrate polymer pairs having the least affinity, and thus being the most useful as a release liner. Horvath Szabo et al. [US 2009/0114387 A1] utilize molecular modeling to calculate the physicochemical property of certain compounds useful for producing heavy oil from an underground reservoir. The authors use semi-empirical or ab-initio calculations to modify the molecular model of the compound and predict its optimized physiochemical properties.

The Molecular Dynamics approach can be useful for understanding processes taking place in the reservoir during oil recovery. In particular it provides the possibility to estimate the surface/interfacial tension in systems of different topology [1]. Attempts to understand details of interaction between component at oil-water; oil-solid matter and water-solid matter surfaces have been performed by means of the Molecular Dynamics approach by a number of authors.

Connoly et al [2] used molecular dynamics to study the thermal behavior of hexane layer on graphite surfaces in the framework of a fully atomistic description. The same system has been investigated by Peters and Tildesley [3] and by Wexler with co-workers [4, 5] in the framework of the so-called united atom approach.

A fully atomistic molecular dynamics approach has been applied to investigate aggregation dynamics of asphaltenes [6] and asphaltenes and resins in toluene and heptane [7, 8]. And a multi-scale approach with fully atomistic [9] or coarse-grained [10] representations of heavy components has been presented with the effective solvent simulated as a continuum media (background field). A highly coarse-grained approach was used in [11] to consider aggregation and deposition of asphaltenes in a capillary flow. Fully atomistic simulations of asphaltenes in water-toluene/heptane systems were performed in [12]. A mesoscopic model was used to investigate behavior of asphaltenes and resins in crude oil [13].

Effects at water/oil interfaces have been studied at high resolution by number of researchers [14, 15]. And the role of surfactants in modifying properties of water-oil interfaces has also been investigated by Molecular Dynamics simulation at different levels of detail, from a fully atomistic descriptions of the components [16, 17] and united atom descriptions [18] up to highly coarse-grained models [19, 20, 21].

Recently, studies of water-oil-surfactants/additives (CO2) mixtures near different solid surfaces, such as calcite [22, 23] or graphite [24], were reported which reproduced adsorption dynamics at molecular scale.

In the light of the known methods it is seen as an object of the present invention to provide a method of using Molecular Dynamics simulation for analyzing Oil-Brine-Rock systems in order to predict the efficiency of potential additives.

SUMMARY OF INVENTION

The present invention provides methods for selecting an additive for enhanced recovery from a subterranean hydrocarbon reservoir. The methods include using parameters characterizing rock type and surfaces in the reservoir, pore geometry and/or distribution, hydrocarbons and/or other constituent elements identified as being present in the reservoir, using parameters characterizing an injection fluid or fluid mixture to be injected into the reservoir, using parameters characterizing the additive to be added to the injection fluid and its concentration; using the parameters to determine at a first level of molecular dynamic modeling the effect of the additive on the interfacial tension between hydrocarbon and water/brine or an equivalent parameter, using the parameters and results derived from the first level of molecular dynamic modeling to determine at a second coarser level of molecular dynamic modeling wettability effects or an equivalent parameter and using the parameters and results derived from first and second level of molecular dynamic modeling to determine at a third coarser level of molecular dynamic modeling imbibition or drainage effects.

The levels chosen to model the system in decreasing details are best selected to match the level of detail required with existing computing power and time constraints. In a preferred embodiment of the invention, the three levels are set at least approximately at levels known in Molecular Dynamics as "fully atomistic", "united atom model" and "coarse-grained".

The determination of which of the parts of the downhole system to be reproduced is a constituent element required to be represented in the molecular model depends on the desired level of accuracy and time and resources constraints.

In further preferred embodiments, fully atomistic models are utilized to evaluate the effect of different additives on the interfacial tension between the brine and the oil. Interaction between different oil components brine components and additives with rock surface are analyzed in detail. After the role of each components in the system is clarified, stages of coarser graining procedure are applied.

In a preferred embodiment the second level is the level of united atom model. At this level, one simulation particle represents a group of individual atoms thus up-scaling each individual component to less detailed level of description. Capillary wettability is best implemented at this level in the model by effective interaction potential between united atom particles representing fluids and particles representing matrix surface.

In a further preferred embodiment, modeling of the imbibition process or diffusion process is simplified by moving to the level of even fewer effective components or coarse-grained simulation. The impact of all individual components (salt ions and other species) is taken into account by interaction potentials. This up-scaling facilities the evaluation of the dynamics of imbibition/drainage at the pore scale, in turn providing a measure for the efficiency of the additives.

These and other aspects of the invention are described in greater detail below making reference to the following drawings.

DETAILED DESCRIPTION

In the following example of the invention a method is described aimed at analyzing directly the effect of chemical additives in water injected into an oil reservoir to move the oil out from porous rock. It is well known that the interfacial tension between oil and brine and the relative adherence of oil or water to the rocks (wettability) can be modified with specific chemical additives such as surfactants. However since rock, oil and brine differ from one reservoir to another and from one layer to the other in each reservoir, it is regarded as a difficult problem to identify a suitable chemical additive and to determine its minimal concentration to lower the rock wettability to oil and to reduce the oil/brine interfacial tension. In this example of the invention this problem is addressed using a staged process based on Molecular Dynamics modeling.

Figure 1:
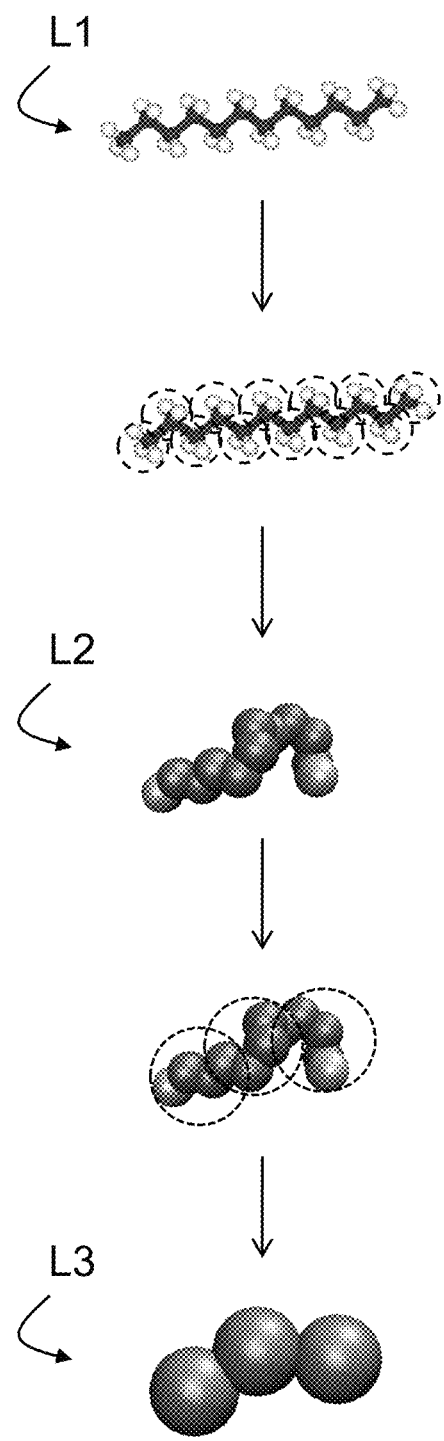
FIG. 1 illustrates modeling effects as used in an example of the invention.

An example of a component or constituent element of the system represented at three different molecular stages or levels is shown in FIG. 1. The species modeled is dodecane.

At the first level L1, which in the illustration is the atomistic level, —the molecule is represented by its full set of constituent atoms and their interactions. At the second coarser level L2, or united atom model, one simulation particle represents a group of atoms, such as methyl or methylene groups as in the present example. This level L2 is used to confirm that the impact of each individual component or constituent element has been understood correctly in the framework of the atomistic model and the system can be up-scaled to a less detailed level of description. At the third, even coarser level L3, the coarse-grained level, the groups of atoms are again regrouped to represent larger sections of atoms or full molecules for a dynamic simulation of the processes.

As will become apparent from the following description, the first two levels L1, L2 are used in this example to determine static properties such as interfacial tensions between components (oil, brine, gas, rock) and wetting or contact angles between fluids and rock. At the third level L3 the system is accessible to modeling of the time evolution of the diffusion process.

It is worth noting that for the purpose of the invention the restriction to three levels and the particular choice of these levels is a matter of computational efficiency. However there may be reasons to distribute the process over more than three levels or setting the levels at different degrees of granularity than proposed in this example.

Figure 2A:
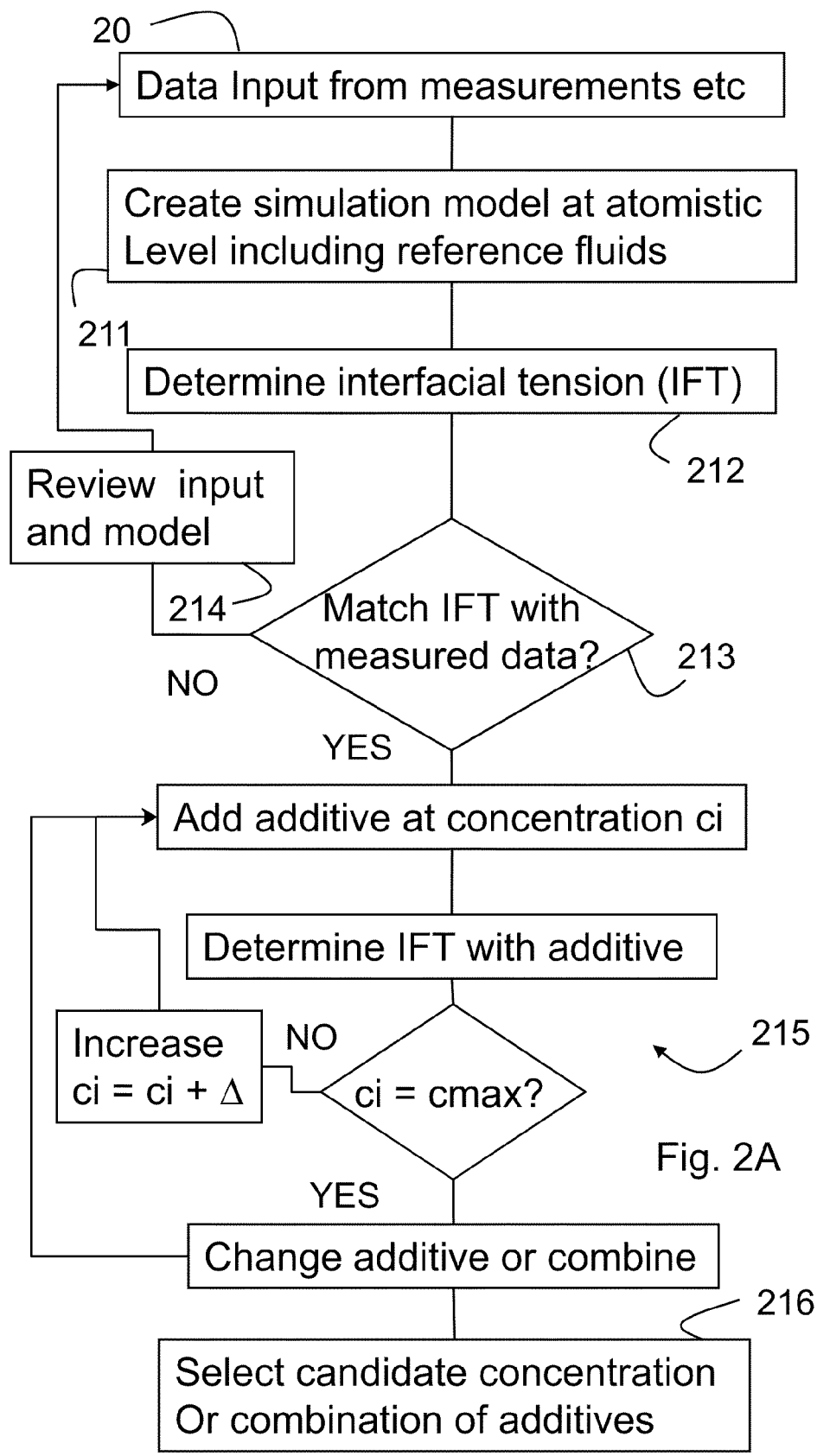
FIGS. 2A-2B illustrate steps of a method in accordance with an example of the invention.
Figure 2B:
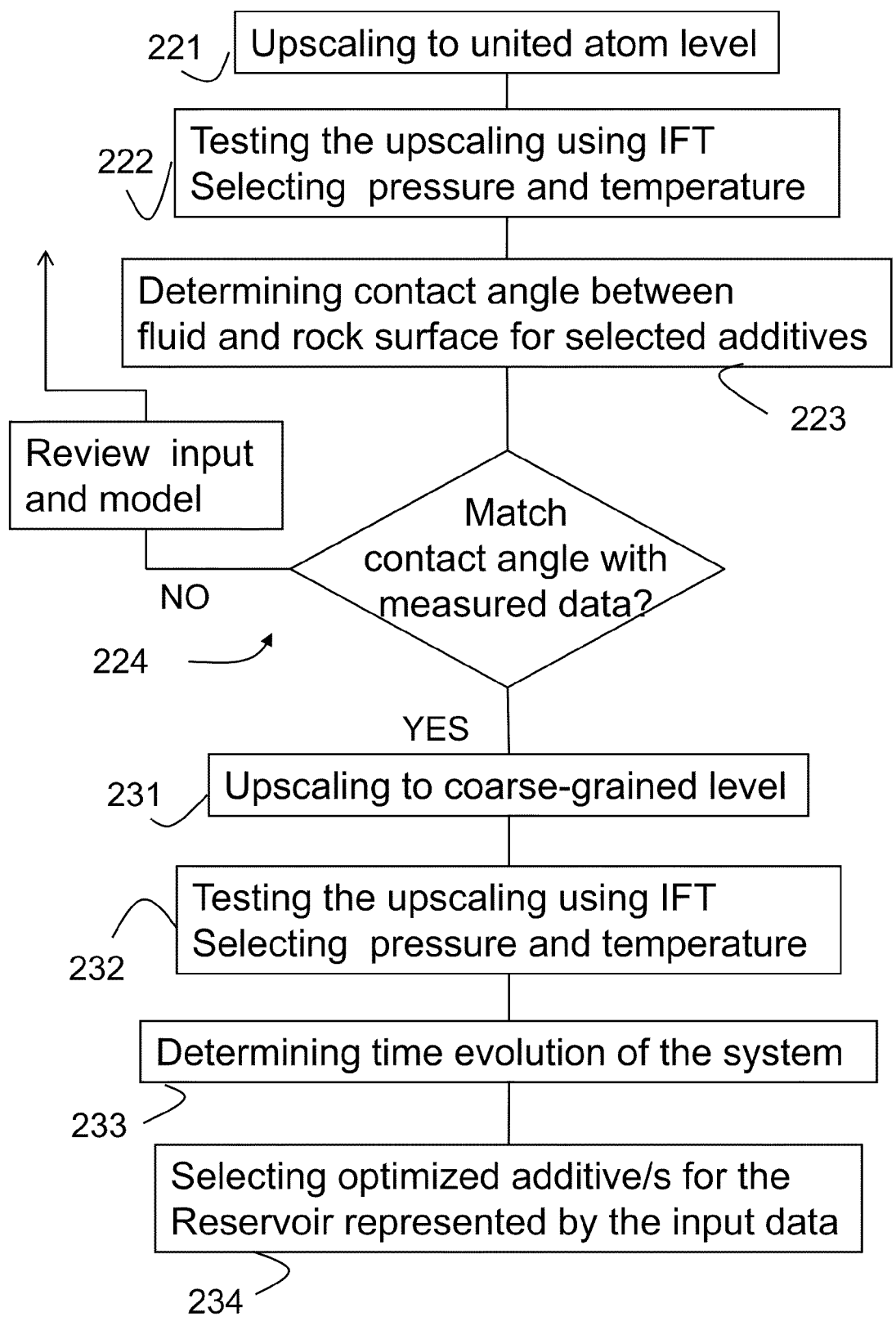

In the following the effects additives have on the imbibition of the formation are modeled using the above three level approach. Steps of the example are shown in the flowcharts of FIGS. 2A and 2B.

After evaluation and preparing the input data (Step 20), a simplified representation of the subterranean environment is built 211 for use as test bed to model the effectiveness of additives.

The input parameters to this staged process can be obtained from standard oil field measurements ranging from geological surveys including logging data to laboratory analysis preformed for example on cuttings, cores, downhole fluid samples and the like. The input parameters are designed to provide the modeling process with parameters describing for example:

Rock mineralogy, Brine, Oil, Gas chemistry (Asphaltenes, Resins, Aromatics etc)

Reference injection fluids (without additives): sea water, fresh water, CO2, methane etc.

Relevant available additives (surfactants, salts of any kind, polymers, CO2 etc)

Characteristics of pore rock dimension/pore geometry (given by rock cores, pore spectrum and Rock Typing like NMR-T2 distribution, micro-computed tomography, and high-resolution confocal microscopy)

In the example the simplified representation is a volume consisting of two pores connected by a capillary or pore throat and embedded within a rock surface. If the capillary wall is set as oleophilic or hydrophilic the brine will or will not push the oil from the capillary by natural imbibition as governed by diffusion processes. The rock properties (Carbonates, Dolomite, Sand stone, Shales, Clay content . . . ) are reconstructed from atomistic level and allow the parametric study of the global attributes of the chemical stability of the reservoir.

In the pore model of this example the Peclet number is small and due to the size of the pore system priority is given to diffusion effects, however the present example can in principle be extended to include further force fields as such caused by a pressure gradient.

At the initialization one pore is filled with water, which can be either pure, a brine with known ion concentration or reconstituted formation water. Given the complexity of many hydrocarbon reservoirs, a restricted or simplified reconstitution may be chosen to reduce the number of constituent elements in the model system. The other pore is filled with the formation hydrocarbons as reconstituted from downhole or surface measurement such as spectroscopic or chromatographic measurements. The pore throat at the initial moment can be filled either with oil assuming an oil wet rock surface or with water. The former case is for example of interest when investigating the effectiveness of oil recovery agents while the latter case can be of interest for reproducing imbibition/drainage curves. Additional components such as asphaltenes can be placed in the pore throat to adopt the modeled scenario to real formation conditions as apparent from the downhole measurements.

This initial model is verified (Step 213) and, if required, modified (Step 214) using an atomistic level calculation (Step 212) of the interfacial tension (IFT) and a comparison with measurements.

Once the matching of IFTs is found to be acceptable, the effects of a first of a series of additives is modeled in several model runs at increasing concentrations (Step 215) remaining at the fully atomistic level L1 and hence mirroring the initial calculations as described above. The results of these calculations reflect the influence of the ions or surfactants on the IFT for various concentrations of the additive and/or mixture of additives. The effect of injected ions and chemical species can be optimized by repeatedly running the model ultimately resulting in a candidate list of effective additives or mixture and their respective concentrations (Step 216).

At this first level fully atomistic models are used to evaluate the effect of different additives: salt ions (Na+, K+, H+Cl−, . . . ), surfactants, and other surface active species on the interfacial tension between the brine and the oil. To accelerate this stage the calculation is best limited to the interfacial tensions at interfaces between the fluid components. Also at this stage the interaction between different oil components (asphaltenes, resins, carboxylic acid, etc.), brine components and additives with rock surface is analyzed at atomic level. The calculation of the IFT through molecular dynamic modeling at atomistic level can be performed using various methods known per se. Force fields for atoms and molecules are published for example on the website of the AMBER organization currently at http://ambermd.org/#ff. With the knowledge of such force fields, the interface between the fluids can be treated as a layered structure with periodic boundary conditions. From such a view point the tension at an interface can be obtained from the anisotropy of the pressure as described for example by Nijmeijer et al [25]:

$$\gamma = \frac{1}{2L_x L_y}\left(\langle J_{zz}\rangle - \frac{1}{2}(\langle J_{xx}\rangle + \langle J_{yy}\rangle)\right) \quad (1)$$

where $J_{ij}$ is the component of the stress tensor and $L_i$ is the length of the system in the corresponding direction.

After the role of each components in the system is clarified two following stages of coarser graining procedure can be applied. For these investigation at coarser levels a selection is made (Step 216) out of many potentially effective additives and/or their mixtures and passed on as input to the coarser levels L2 and L3. The selection criteria can be based in the simplest case on the highest efficiency of reducing (or increasing) the IFT, but is more likely to involve a set of criteria including costs, environmental and other operational considerations.

An example of steps performed at the coarser levels L2 and L3 are shown in FIG. 2B. At the stage L2 components of the model are scaled up to the united atom model (Step 221). This upscaling operation replaces the atomistic description of the interaction of the molecules with effective potentials describing the interactions of a group of atoms. If not introduced in the previous L1 stage as atomistic model, it is at this stage that a molecular description of the rock surface is introduced. To ensure consistency between the atomistic calculation at the L1 stage and this stage L2, the IFT between the oil and water interface is recalculated (Step 222). The potentials which are introduced when moving from the atomistic model to the united atom model are adjusted until the IFT is equal for both levels.

Once consistency is achieved, an estimate of the wetting or contact angle at the surface of the capillary is reproduced with the selected most promising additives (Step 223). To reproduce the contact angle, a drop of the fluid at the surface (in the presence of the second fluid or without it) is modeled and the drop shape is approximated (averaged over time) by a spherical arc, the tangent of which at the surface equals the contact angle. The surface tension is adjusted until the contact angle matches the contact angle as measured from experiments (Step 224). Then the L3 or coarse-grained modeling is applied (Step 231).

At the coarse-grained level the IFT and the contact angles are reproduced in order to establish consistency between all three levels of modeling (Step 232). Once the desired consistency is achieved, the coarse-grained or L3 simulation traces the process of imbibition or oil recovery at molecular scale and is used to evaluate the efficiency of different additives. As mentioned above, the modeling of natural oil/imbibition-water/drainage of the pore system in this example is driven by diffusion effects, but can be extended to include further driving forces. At the coarse L3 level of molecular dynamic modeling the current computing resources are sufficient to model dynamic behavior or time evolution of the whole capillary for time periods equal to the diffusion time through the capillary volume (Step 233). The modeling techniques required to model the diffusion process at the coarse-grain level are known per se. Examples of these methods are described by D. I. Dimitrov et al [26], G. Martic et al [27] and S. Ahadian et al. [28].

Figure 3:
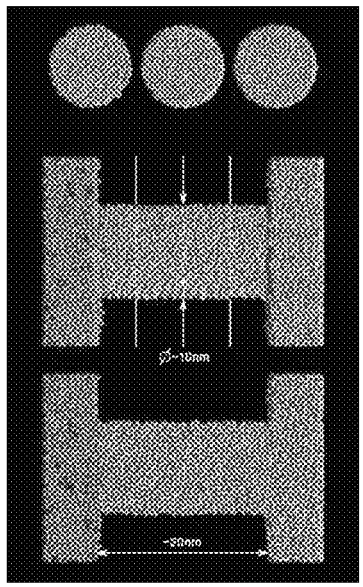
FIG. 3 illustrates results of a coarse-grain simulation.
Figure 3:
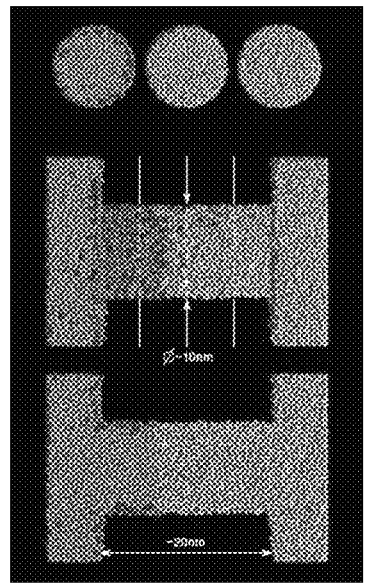
Figure 3:
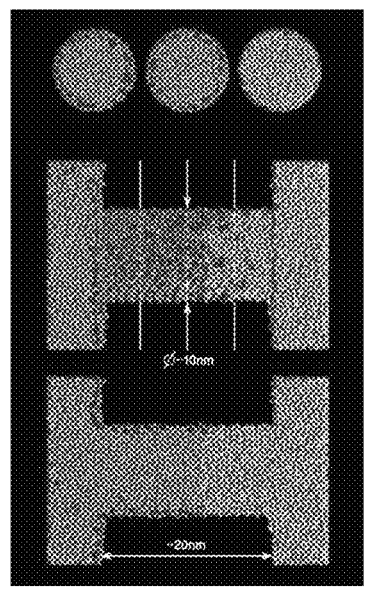
Figure 3:
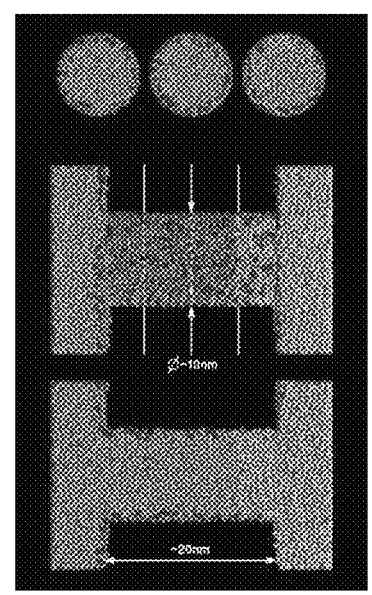

An example of the time evolution of a surfactant water system diffusing into an oil-filled capillary is illustrated by the sequence of the four panels of FIG. 3. The panels show the gradual replacement of oil (on the right side) by a brine/surfactant mixture (from the left side) by the modeled diffusion process.

By monitoring the time evolution and results of the diffusion processes for different additives, their mixtures and concentrations, it is possible to determine a most efficient additive or a combination of additives and an optimized concentration (Step 234).

Depending on the desired complexity and available computing resources the results can be either relative providing a relative ranking between the various scenarios of chemical additives or they can be absolute thus making enabling quantitative estimates with or without calibration to the external data. This simulation can be performed at different temperatures and at different pressures gradients which can provide additional information about dynamics of the imbibition process and thus allow optimizing the additive injection procedure. In the framework of the suggested model enforced imbibition can be considered as well by applying external force (pressure) to particles on one of the reservoirs.

It is also possible to extend the results as gained from the methods in accordance with the present invention to a larger scale using for example statistical descriptions of the pore space in the formation as determined from measurements. If, for instance, a microscopic volumetric sweep efficiency is calculated using the present method, the upscaling can yield a macroscopic recovery factor based on an water flood operation using the selected additive.

While the invention is described through the above exemplary embodiments, it will be understood by those of ordinary skill in the art that modification to and variation of the illustrated embodiments may be made without departing from the inventive concepts herein disclosed. Moreover, while the preferred embodiments are described in connection with various illustrative processes, one skilled in the art will recognize that the system may be embodied using a variety of specific procedures and equipment and could be performed to evaluate widely different types of applications and associated geological intervals. Accordingly, the invention should not be viewed as limited except by the scope of the appended claims.

What is claimed is:

1. A computer-implemented method of selecting an additive for enhanced recovery from a subterranean hydrocarbon reservoir comprising the steps of: using a set of said parameters to determine, at a first level of molecular dynamic modeling, an effect of said additive on interfacial tension between hydrocarbon and water/brine wherein the first level includes an atomistic representation of constituent elements, wherein the set of parameters includes:
   a first parameters characterizing at least one of (1) rock type and surfaces in the reservoir, (2) pore geometry (3) pore distribution, (4) hydrocarbons, or (5) other constituent elements identified a being present in said reservoir;
   a second parameter characterizing an injection fluid to be injected into said reservoir; and
   a third parameter characterizing (1) said additive to be added to said injection fluid and (2) a concentration of the additive;
   a fourth parameters setting a temperature and pressure;
   using said set of parameters and said effect of said additive on interfacial tension derived from said first level of molecular dynamic modeling to determine, at a second coarser level of molecular dynamic modeling wettability effects, wherein the second level includes united atom models constituent element; and
   using said a set of parameters and said effect of said additive on interfacial tension derived from said first level of molecular dynamic modeling and said wettability effects derived from said second level of molecular dynamic modeling to determine, at a third coarser level of molecular dynamic modeling, imbibition or drainage effects, where the third level includes a coarse-grain model of constituent elements; and
   wherein interfacial tensions are determined at the first, second and third level of molecular modeling based on the effects of wettability and drainage or imbibition at each level of molecular dynamic modeling and wherein parameters are altered to match interfacial tensions between the first, second and third levels of molecular dynamic modeling.

2. The computer-implemented method in accordance with claim 1, wherein the additive is changed to test a plurality of possible additives.

3. The computer-implemented method in accordance with claim 1, wherein the concentration of the additive is altered to test a plurality of possible concentrations.

4. The computer-implemented method in accordance with claim 1, wherein the additive and its respective concentration are altered to test a plurality of additives, their mixtures and their respective possible concentrations.

5. The computer-implemented method in accordance with claim 1, wherein the additive and/or its respective concentration is altered to test a change of interfacial tension for a plurality of additives, their mixtures and/or their respective possible concentrations at the first level.

6. The computer-implemented method in accordance with claim 5, wherein a pre-selection from a plurality of additives, their mixtures and/or their respective possible concentrations is made based on results obtained at the first level.

7. The computer-implemented method in accordance with claim 1, wherein the interfacial tension or the equivalent parameter determined at the first level is compared to measured data.

8. The computer-implemented method in accordance with claim 1, wherein the wettability effect or the equivalent parameter determined at the second level is compared to measured data.

9. The computer-implemented method in accordance with claim 1, wherein only static parameters are determined at the first and second level.

10. The computer-implemented method in accordance with claim 1, wherein a time evolution of results are determined at the third level.

11. The computer-implemented method in accordance with claim 1, wherein at the second coarser level wettability is represented by contact angle values.

12. The computer-implemented method in accordance with claim 1, wherein the results are combined with a statistical description of the pore network to determine a recovery factor.

* * * * *